(12) United States Patent
Gournay et al.

(10) Patent No.: US 6,478,795 B1
(45) Date of Patent: *Nov. 12, 2002

(54) TORQUE LIMITING CLAMPING PLUG FOR OSTEOSYNTHESIS INSTRUMENTATION

(75) Inventors: Jose Gournay, Berck Plage; Dominique Petit, Berck sur Mer; Jean Saurat, Etaples, all of (FR)

(73) Assignee: Sofamor S.N.C., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/634,028
(22) PCT Filed: Aug. 24, 1995
(86) PCT No.: PCT/FR95/01115
§ 371 (c)(1), (2), (4) Date: Sep. 23, 1996
(87) PCT Pub. No.: WO96/06576
PCT Pub. Date: Mar. 7, 1996

(30) Foreign Application Priority Data

Aug. 29, 1994 (FR) .............................................. 94 10377

(51) Int. Cl.⁷ .............................................. A61B 17/56
(52) U.S. Cl. .............................. 606/61; 606/72; 606/73; 411/5
(58) Field of Search ............................ 606/73, 72, 61; 411/2, 3, 1, 5, 404, 393

(56) References Cited

U.S. PATENT DOCUMENTS

| 791,548 A | 6/1905 | Fischer |
| 2,083,054 A | 6/1937 | Cline ........................ 285/139 |
| 2,201,087 A | 5/1940 | Hallowell |
| 2,239,352 A | 4/1941 | Cherry |
| 2,295,314 A | 9/1942 | Whitney |
| 2,532,815 A | 12/1950 | Kindsvatter |
| 2,553,337 A | 5/1951 | Shafer |
| 2,778,265 A | 1/1957 | Brown |
| 2,877,681 A | 3/1959 | Brown |
| 2,927,332 A | 3/1960 | Moore |
| 3,115,804 A | 12/1963 | Johnson |

(List continued on next page.)

FOREIGN PATENT DOCUMENTS

| DE | 3630863 | 3/1988 |
| DE | 3738409 | 5/1989 |
| EP | 0 195 455 | 9/1986 |

(List continued on next page.)

OTHER PUBLICATIONS

Jackson, Roger P., Declaration Under Rule 131, Jul. 24, 1998, from U.S. patent application, Ser. No. 08/778,765, (issued as U.S. Patent No. 6,004,349).

*Primary Examiner*—David O. Reip
*Assistant Examiner*—Julian W. Woo
(74) *Attorney, Agent, or Firm*—Woodard, Emhardt, Naughton, Moriarity & McNett

(57) ABSTRACT

The plug (1) comprises two coaxial parts (2, 3) separated by a fracture initiating line (4). A respective print (6, 7) is provided on each part and is coaxial with the other print. The first part (1) permits the screwing of the second part (3) which is provided with a screw thread (5) in an implant to which it must remain fixed after fracture of the two parts on the line (4), when a predetermined fracture torque is exceeded. The print (7) of the second part (3) permits a subsequent unscrewing, if necessary, for disassembling the instrumentation, which constitutes an essential advantage of this plug. Further, the clamping can be achieved with high precision in conformity with the wishes of the manufacturer, since the fracture torque can be adjusted to the intended value by machining the fracture intiating line (4) in a precise manner.

40 Claims, 6 Drawing Sheets

U.S. PATENT DOCUMENTS

| | | | |
|---|---|---|---|
| 3,143,029 A | | 8/1964 | Brown |
| D200,217 S | | 2/1965 | Curtiss |
| 3,370,341 A | * | 2/1968 | Allsop .......................... 411/2 |
| 3,498,174 A | | 3/1970 | Schuster et al. ................. 31/2 |
| 3,584,667 A | | 6/1971 | Reiland ....................... 145/50 |
| 3,812,757 A | * | 5/1974 | Reiland ......................... 411/2 |
| 3,963,322 A | * | 6/1976 | Gryctko ......................... 411/2 |
| 4,269,246 A | | 5/1981 | Larson et al. ................. 81/460 |
| 4,492,500 A | | 1/1985 | Ewing |
| 4,506,917 A | * | 3/1985 | Arue .......................... 411/393 |
| 4,641,636 A | | 2/1987 | Cotrel ......................... 128/69 |
| 4,763,644 A | | 8/1988 | Webb |
| 4,764,068 A | | 8/1988 | Crispell |
| 4,790,297 A | | 12/1988 | Luque .......................... 128/69 |
| 4,815,453 A | | 3/1989 | Cotrel ......................... 128/69 |
| 4,838,264 A | | 6/1989 | Bremer et al. .............. 128/303 |
| 4,874,275 A | | 10/1989 | Gotman ......................... 411/5 |
| 5,005,562 A | | 4/1991 | Cotrel |
| 5,067,955 A | | 11/1991 | Cotrel ......................... 606/61 |
| 5,073,074 A | | 12/1991 | Corrigan et al. |
| 5,129,388 A | | 7/1992 | Vignaud et al. |
| 5,145,719 A | | 9/1992 | Cotrel ......................... 606/73 |
| 5,147,360 A | | 9/1992 | Dubousset ................... 606/61 |
| 5,261,907 A | | 11/1993 | Vignaud et al. ............... 606/60 |
| 5,261,912 A | | 11/1993 | Frigg .......................... 606/61 |
| 5,282,707 A | | 2/1994 | Palm |
| 5,312,404 A | | 5/1994 | Asher et al. ................... 606/61 |
| 5,346,493 A | | 9/1994 | Stahurski et al. ............. 606/61 |
| 5,364,400 A | | 11/1994 | Rego, Jr. et al. |
| 5,382,248 A | | 1/1995 | Jacobson et al. |
| 5,385,583 A | | 1/1995 | Cotrel ......................... 623/17 |
| 5,487,742 A | | 1/1996 | Cotrel ......................... 606/61 |
| 5,496,321 A | | 3/1996 | Puno et al. ................... 600/61 |
| 5,499,892 A | | 3/1996 | Reed |
| 5,507,747 A | | 4/1996 | Yuan et al. |
| 5,697,929 A | * | 12/1997 | Mellinger ................... 606/73 |

FOREIGN PATENT DOCUMENTS

| | | |
|---|---|---|
| EP | 0 172 130 | 2/1987 |
| EP | 0 276 153 | 7/1988 |
| EP | 0 465 158 | 1/1992 |
| EP | WO 94/10927 | 5/1994 |
| FR | 246312 | 5/1981 |
| GB | 203508 | 9/1923 |
| WO | WO 92/03100 | 3/1992 |
| WO | WO 94/10944 | 5/1994 |

* cited by examiner

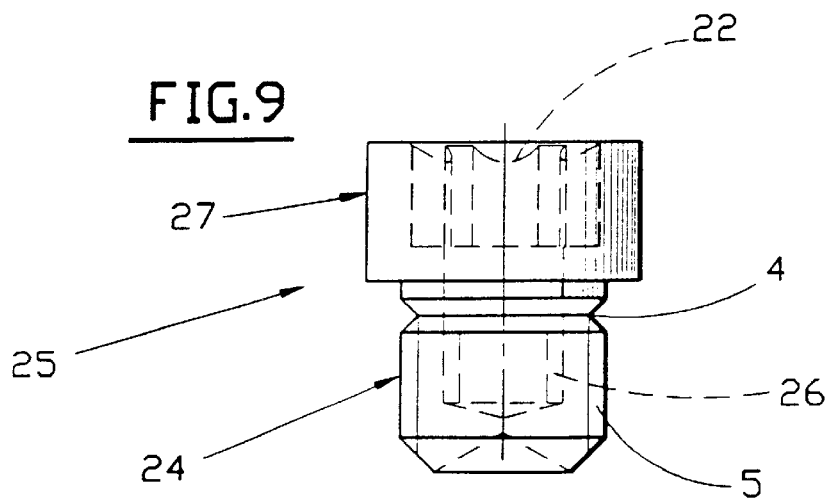
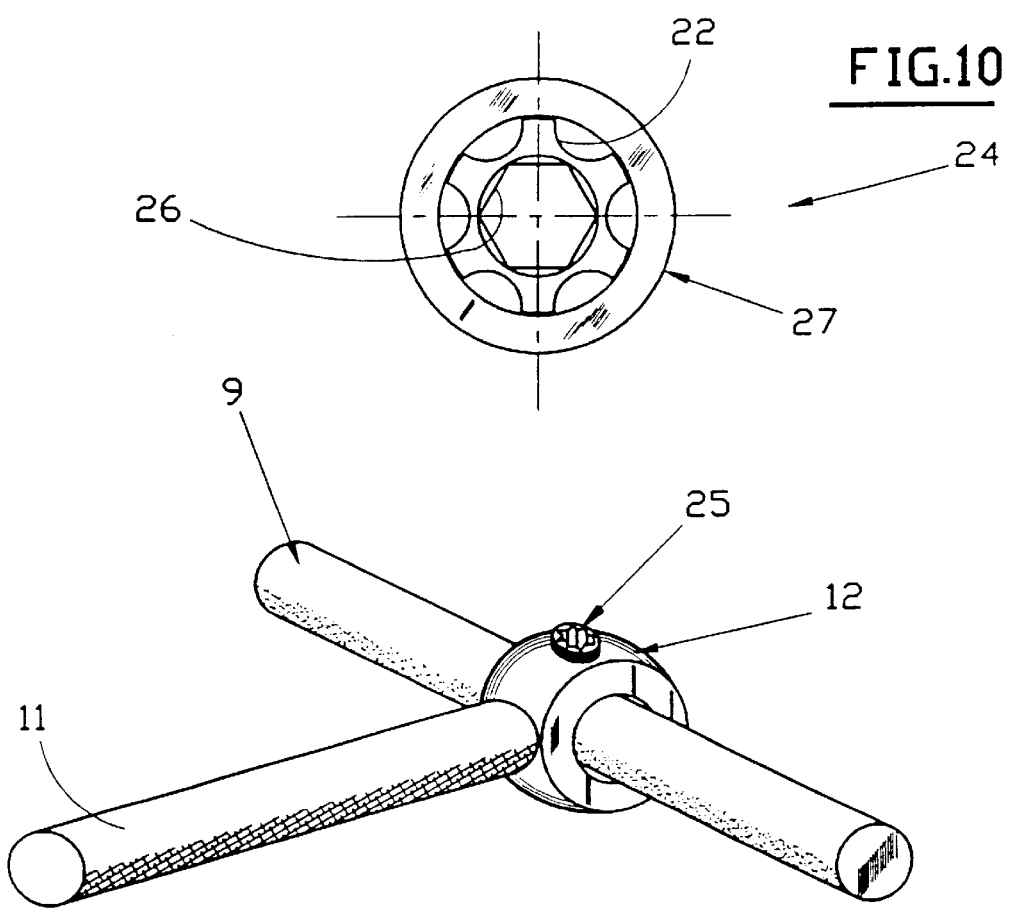

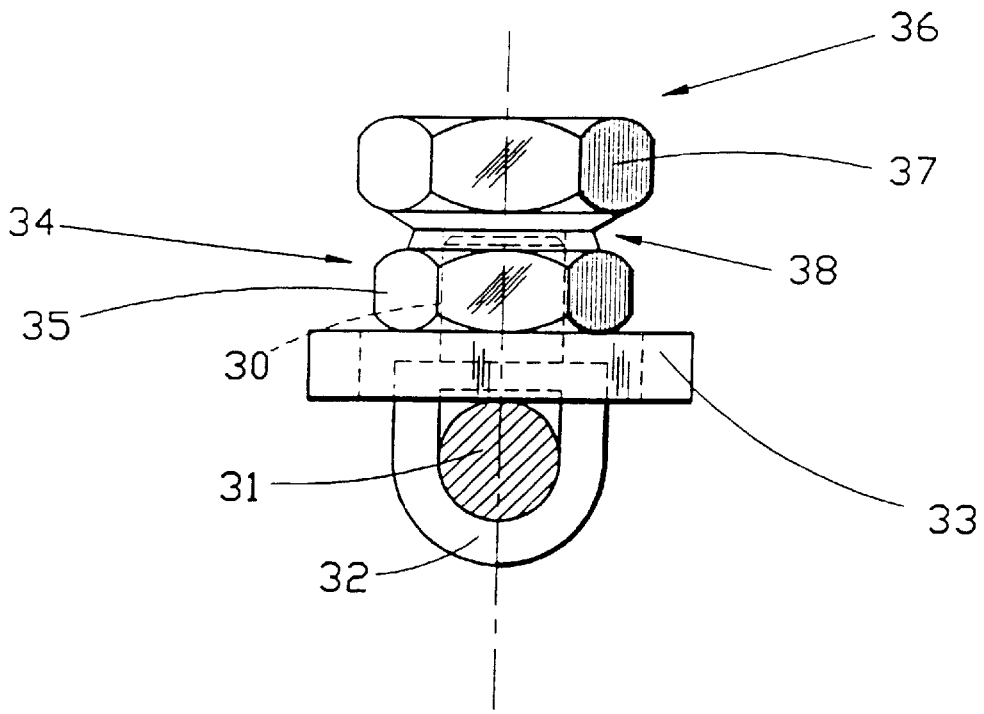
FIG.12
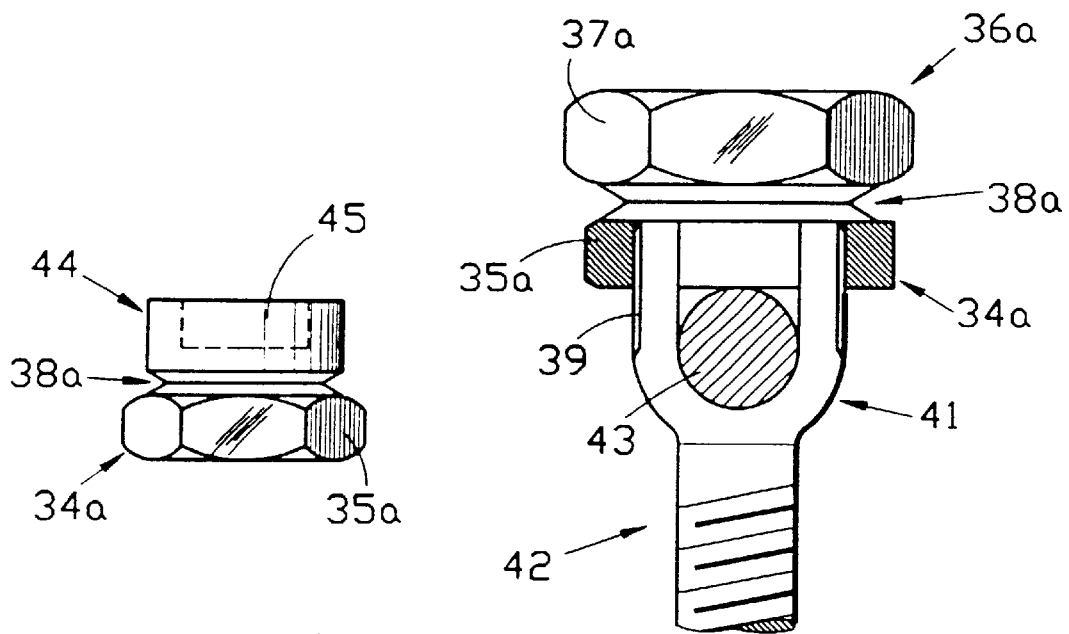
FIG.14
FIG.13

TORQUE LIMITING CLAMPING PLUG FOR OSTEOSYNTHESIS INSTRUMENTATION

The present invention relates to a threaded clamping plug for interconnecting two implants of a spinal osteosynthesis instrumentation or other implants.

In spinal osteosynthesis instrumentations heretofore employed, in particular those of the "COTREL-DUBOUSSET" type (U.S. Pat. Nos. 4,641,636 and 4,815,453), the component elements are placed in position and assembled by means of small screws. At the end of the screwing, the surgeon causes their fracture so as to remove their head, which requires cutting the rods if it is necessary to proceed to a subsequent removal of the instrumentation which is consequently rendered relatively awkward.

Further, the measurement of the clamping torques of the screws requires additional instruments the precision of which is not always satisfactory.

Objects of the invention are to provide, on one hand, an assembling element which allows an easier subsequent disassembly of the instrumentation if need be and, on the other hand, a system integrated with the plug which affords a precise predetermined clamping torque.

According to the invention, the threaded plug comprises two coaxial parts separated by a fracture initiating line, and each part is provided with a print coaxial with the other print, the first part being adapted to permit the screwing of the second threaded part on an implant up to a predetermined fracture torque between the two parts, the print provided on the second part permitting an optional subsequent unscrewing of the latter.

The threaded part may be screwed in a tapped hole provided in the corresponding implant, or on the screw thread of the body of a vertebral anchorage element (screw or hook) to ensure the connection of this element with a rod, or on a threaded rod of a transverse connection device between two longitudinal osteosynthesis rods.

It must be understood that these three embodiments of the plug according to the invention are not intended to be limitative, since the invention has a very wide scope in osteosynthesis instrumentations.

Thus, after fracture, when the prescribed torque is exceeded and the two parts are separated, the second part can be if necessary unscrewed by means of its print which is adapted to a suitable tool so that the device can be disassembled.

The magnitude of the fracture torque is a function of the depth of the fracture initiating line and can be easily adjusted to the desired magnitude. It is therefore possible to obtain for the clamping torque an improved precision relative to clamping torques employed up to the present time with the usual screws, since it is possible to determine the fracture torque in a much more precise manner than with the usual means which involve the use of a relatively imprecise torquemeter.

Further features and advantages of the invention will be apparent from the following description with reference to the accompanying drawings which illustrate several embodiments thereof by way of non-limitative examples.

FIG. 9 is an elevational view to an enlarged scale of a fourth embodiment of the plug according to the invention.

FIG. 10 is a top plan view of the plug of FIG. 9.

FIG. 11 is a partial perspective view of an instrumentation illustrating an example of the use of the threaded plug according to the invention.

FIG. 12 is an elevational view partly in section to an enlarged scale of a fifth embodiment of the plug according to the invention and of a corresponding instrumentation using this plug.

FIG. 13 is an elevational view partly in section to an enlarged scale of a third example of the use of the plug according to the invention.

FIG. 14 is an alternative embodiment of the plug of FIG. 13.

Figure 1:
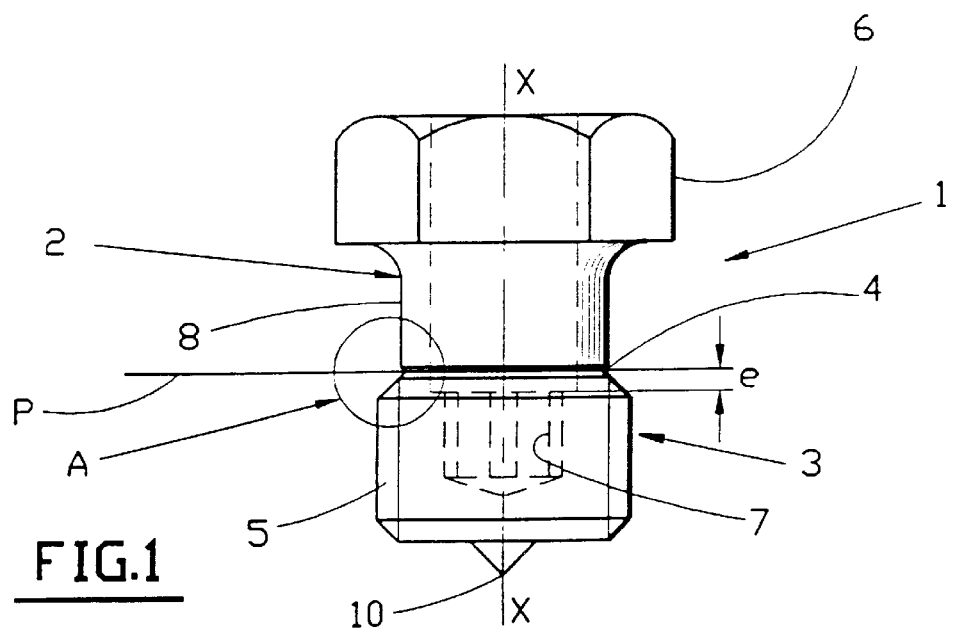
FIG. 1 is an elevational view to an enlarged scale of a first embodiment of the threaded plug according to the invention.
Figure 2:
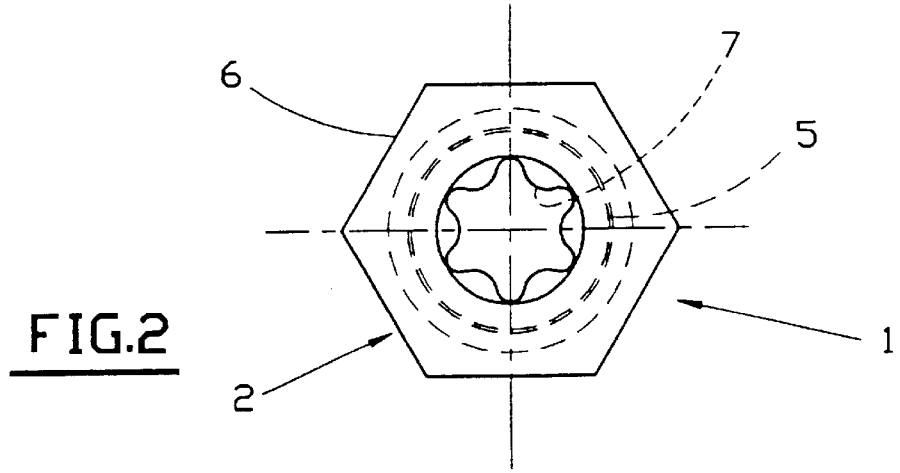
FIG. 2 is a top plan view of the plug of FIG. 1.
Figure 3:
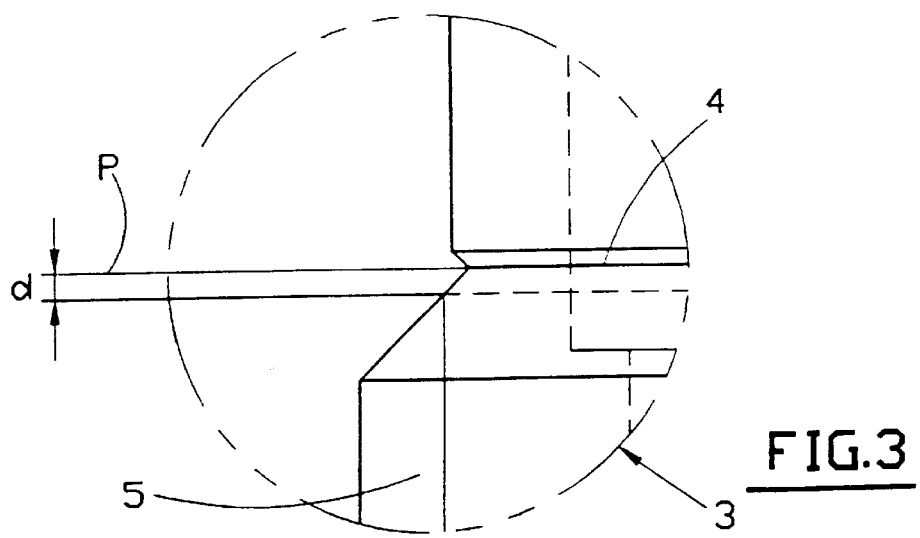
FIG. 3 is a partial elevational view to an enlarged scale of the detail A of FIG. 1.

With reference to FIGS. 1 to 3, there is shown a clamping plug 1 for providing a connection between two component implants of a spinal osteosynthesis instrumentation, not shown, for example of the type illustrated in the aforementioned patents.

The plug 1 is constituted by two coaxial parts 2, 3 separated by a fracture initiating line 4. The part 1, which is unthreaded, constitutes the clamping or tightening head of the plug, while the part 3 is provided with an outer screw thread 5 and is adapted to be embedded in an element to be assembled with another element onto which the threaded part 3 must be clamped.

The first part 1 is provided with a hexagonal exterior print or impression 6 having an axis XX which is the general axis of the plug 1. A second print or impression 7, which is different from the print 6, hexalobate in the illustrated embodiment and coaxial with the hexagonal print 6, is formed in the second part 3 beyond the fracture line 4.

The print 6 is connected to a smooth cylindrical part 8 connected to the second part 3, the fracture initiating line 4 being machined at the end of the part 8. A predetermined offset e is provided between the plane P of the fracture line 4 and the beginning of the print 7 of the second part 3, which is so dimensioned as to be capable of being embedded in the implant at the end of the screwing. Further, the screw thread 5 of the second part 3 stops just short of the fracture initiating line 4 from which it is spaced by a distance d (FIG. 3). The fracture initiating line 4 is constituted by a groove having a depth corresponding to the predetermined magnitude of the fracture torque. The latter and the unscrewing print 7 of the second part 3 may be advantageously so designed that this print 7 cannot withstand a clamping torque higher than the fracture torque so as to preclude any attempt to pursue the clamping or tightening of the part 3 after fracture of the plug.

The use of the plug 1 just described is clear from the foregoing description. The screwing of the part 3 into the implant is effected by means of a tool, not shown, cooperating with the hexagonal print 6, the fracture between the two parts 1 and 3 occurring at the level of the initiating line 4 as soon as the prescribed maximum clamping torque is reached.

The offset e between the plane P of the fracture line 4 and the beginning of the print 7 of the clamping part 3 has the advantage of preventing the print 7 from being damaged upon fracture, as would be the case if no space was provided between the plane P and the beginning of the print 7. In this way there can be obtained a clean fracture of the head of the plug leaving a smooth surface which has a constant torque and is not aggressive for the intervening personnel.

Further, the fact that the thread 5 of the unscrewing screw stops just short of the fracture initiating line avoids the creation, upon fracture, of a burr at the beginning of the thread 5. Indeed, such a burr should be avoided, since it is painful to the patient and might damage the gloves of the surgeon; on the contrary, a smooth and clean fracture should be obtained.

The hexalobate contour of the interior print 7 is particularly advantageous with respect to other print types owing to its high strength which avoids its deformation. In a general way, prints of revolution, such as the prints 6 and 7, are preferred to simple screwdriver slots owing to their higher resistance to the force exerted by the tool.

The precision of the fracture torque may be about ±3% depending on the machining tolerances. The magnitude and precision of this torque are obtained by more or less deepening the fracture initiating groove.

This precision is greatly superior to that obtained heretofore with the usual screws employing torquemeters.

Figure 4:
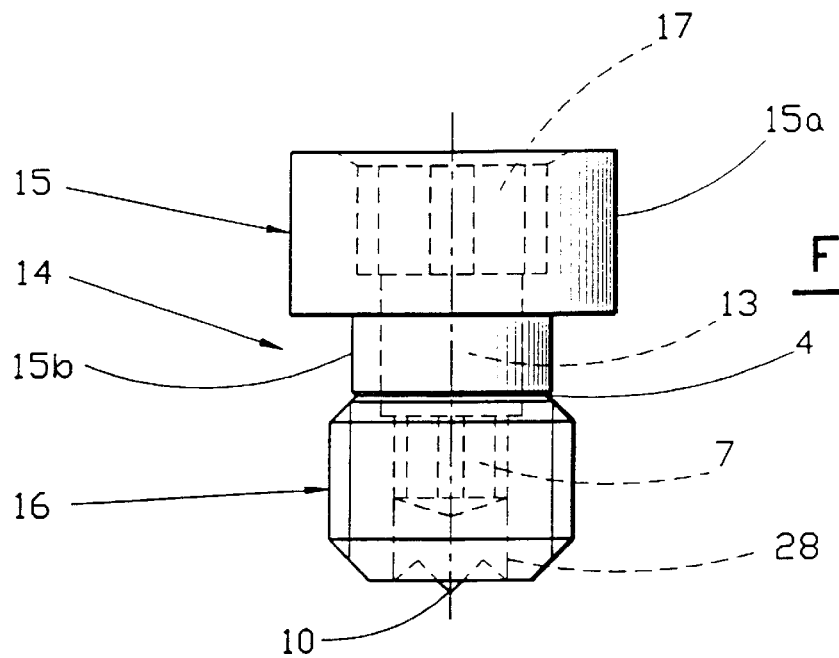
FIG. 4 is an elevational view to an enlarged scale of a second embodiment of the plug according to the invention.
Figure 5:
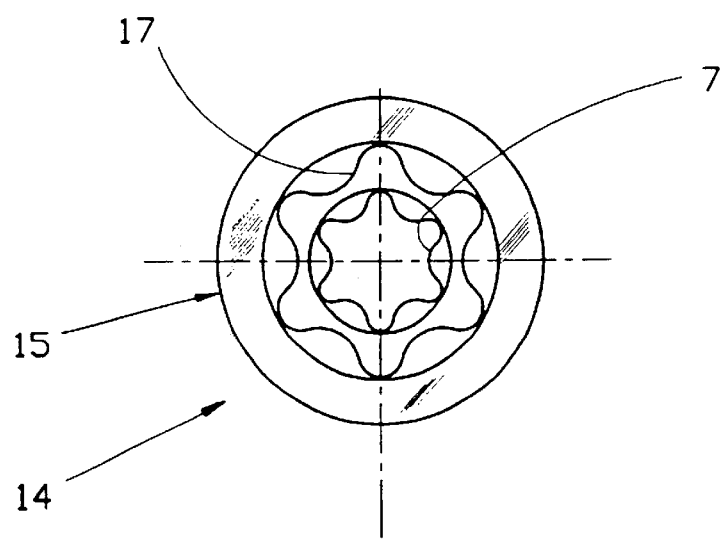
FIG. 5 is a top plan view of the plug of FIG. 4.
Figure 6:
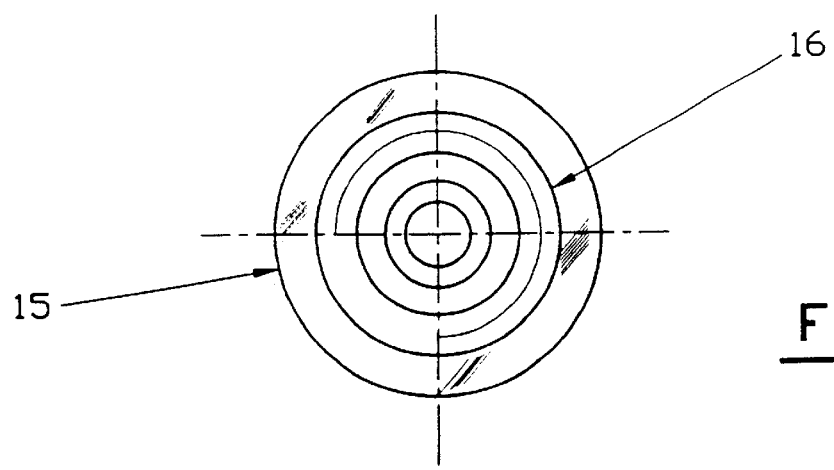
FIG. 6 is a bottom plan view of the plug of FIG. 4.

In the second embodiment illustrated in FIGS. 4 to 6, the plug 14 is constituted in the same way as the preceding plug by two parts 15 and 16. It differs therefrom by the fact that the print 17 of the clamping or tightening part 15 is interior and hexalobate in the same way as the print 7 of the threaded unclamping or unscrewing part 16, the outer surface 15a of the head 15 being smooth. The head 15 is connected by a smooth cylindrical part 15b to the threaded part 16.

Figure 7:
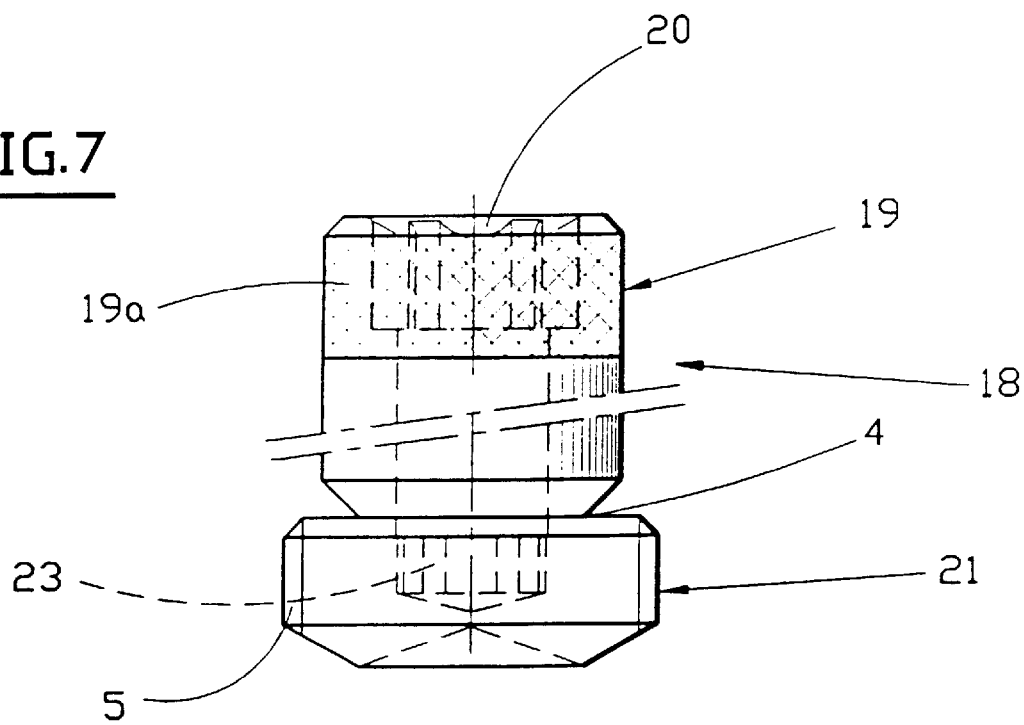
FIG. 7 is an elevational view to an enlarged scale of a third embodiment of the threaded plug according to the invention.
Figure 8:
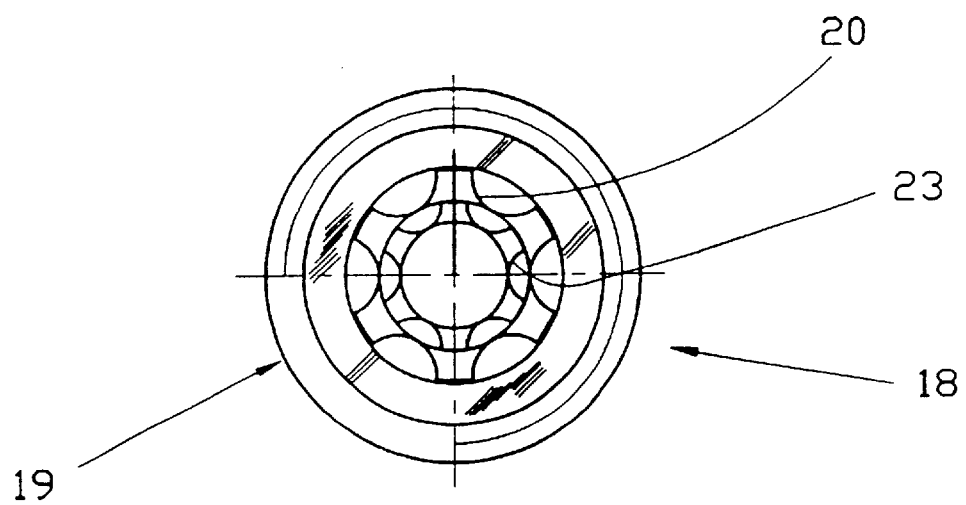
FIG. 8 is a top plan view of the plug of FIG. 7.

In the third embodiment illustrated in FIGS. 7 and 8, the plug 18, formed by two parts 19, 21 separated by the fracture initiating line 4, includes two coaxial interior prints 20 and 23 respectively in the clamping part 19 and the unclamping part 21. The part 19 may carry a knurling 19a permitting a manual positioning and a manual clamping of the plug 18. As a function of the magnitude of the prescribed fracture torque, the positioning and the clamping of the plug 18 may be either exclusively manual by means of the knurled part 19a (or other part) or completed by a mechanical clamping by means of the print 20.

The fourth embodiment illustrated in FIGS. 9 and 10, differs from that of FIGS. 7 and 8 essentially in that there is provided in the unclamping part 24 of the plug 25 a hexagonal print 26 coaxial with the hexalobate print 22 of the clamping part 27.

FIG. 11 illustrates an example of the use of the threaded plug 1 according to the invention. Seen in this FIG. 11 are an osteosynthesis rod 9 associated with a lateral arm 11 at the end of which is fixed a ring 12 through which the rod 9 extends. The rod 9 may have any kind of surface: smooth, a surface having microballs, or asperities, or a screw threaded surface . . . Arranged in the ring 12 is a tapped hole for receiving a threaded plug such as 25 for assembling the rod 9 and the arm 11. This plug 25 (or one of the other described plugs) advantageously replaces the conventional screws employed as described in the aforementioned French patent 92 13476. After separation of its part 27, its remaining part 24 does not extend beyond the implant. Thus, the plug according to the invention advantageously guarantees a small overall size of the instrumentation, since it never protrudes from the part in which it is screwed.

FIG. 12 shows another example of the use of the plug according to the invention in which the implant on which said second part is screwed is a threaded rod 30 of a transverse connection device between two longitudinal osteosynthesis rods of which only one, 31, is shown.

This device comprises a connector 32 through which the associated rod 31 extends and which is connected to the threaded rod 30, and a transverse connection plate 33 which interconnects the rods 31 and through which the threaded rod 30 also extends. There may be screwed on the latter a male nut 34 forming said second unclamping or unscrewing part and having a male print 35 of any shape (hexagonal, square, triangular, notched shape . . . ). The nut 34 is connected to a clamping nut 36 having a male or female driving print of any type. In the illustrated embodiment, this driving print is male owing to a hexagonal exterior print 37. The two nuts 34, 36 are interconnected by a fracture initiating region 38 similar to the preceding regions. This transverse connection device (32, 33, 34) is illustrated by way of a non-limitative example.

Figure 15:
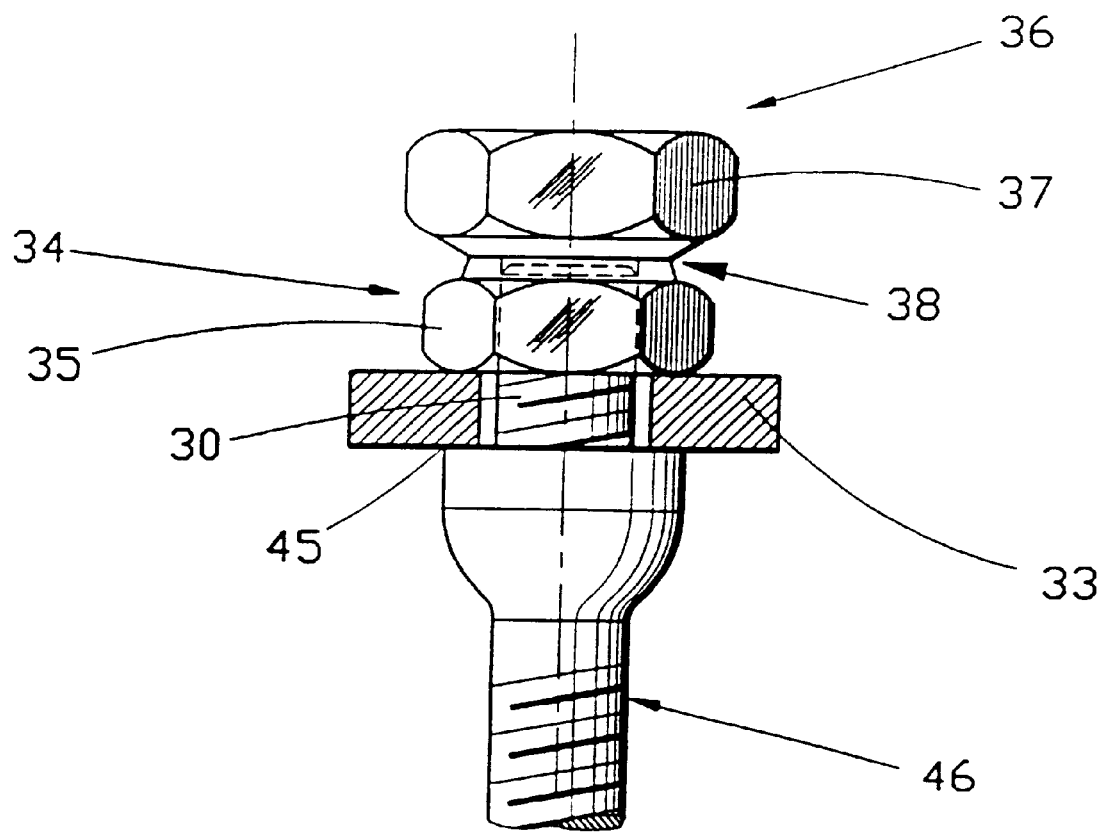
FIG. 15 is an alternative embodiment of the device shown on FIG. 12.

As an example of a possible alternative embodiment (FIG. 15), the plate 33 may bear against a shoulder 45 of a bone screw 46, the plug (36, 34) then permitting the interconnection of these two parts.

FIG. 13 shows another example of the use of the plug according to the invention in which the plug (36a, 34a) which is similar to the plug (34, 36) of FIG. 12 (reference numerals 37a, 34a, 38a, 35a), has its breakable nut 34a screwed on the screw thread 39 of the U-shaped body 41 of a bone screw 42 (or of a hook). After the clamping and the fracture of the zone 38a, the nut 34a then ensures the connection of the screw 42 (or hook) to a rod 43 received in the body 41.

In the alternative embodiment of FIG. 14, the male nut 36a is replaced by a nut 44 having a print 45 of any profile.

It will be understood that the unclamping print 35a may have any shape.

In the various embodiments of the invention, the clamping torque obtained conforms to the wishes of the manufacturer and permits repeating this torque, which is not possible with the currently employed dynamometric clamping means, since the variaion increases with the number of sterilizations of these instruments.

In a general way, any type of print may be employed for the two component parts of the plug with, however, a preference for hexalobate prints. It is in this way possible to provide square, triangular, cruciform prints etc. both for clamping and disassembly, interior and exterior, and any type of fracture initiating profile.

The disassembling print (7, 23 . . . ) may be blind as shown or may open onto the face of said second part facing toward the rod of the instrumentation. Such a print is shown in FIG. 4 which illustrates a through print 28, the point 10 having been eliminated. It permits in this way achieving any type of plug-rod interface (point such as 10 in FIG. 1), cup etc.

The plug may have any diameter and break at any predetermined torque.

Advantageously, an identical standard clamping part may be employed for different types of threaded unclamping or unscrewing part, which simplifies the manufacture of the plug and reduces the cost. Two identical prints separated by a fracture initiating line may also be superimposed. The first part (2 . . . ) may be of any shape, hollow or in relief, and may be for example screw threaded.

It is possible to provide advantageously for the use of an instrument which permits retaining the head (first part) of the plug once it has been broken, or a system for maintaining the head on the screwdriver which prevents the head from falling into the area of operation.

The head of the plug may have a special geometry ensuring the maintenance by clamping means of the broken head, and a manual positioning (FIG. 7). The first part of the plug may be used as an anchoring point of an instrumentation providing a connection between implants for purposes of correction, or distraction or compression. Lastly, in contrast to that which has been illustrated in the drawings, in particular in FIG. 4, where the two prints 17 and 7 open onto an intermediate chamber 13, it is possible to close this chamber. In this case, the print 7 of the clamping part 16 is then replaced by the through part 28.

We claim:

1. A threaded clamping plug for providing an interconnection between two implants comprising:
    a first part having a first outer diameter and a second threaded part having a second outer diameter, said first outer diameter greater than said second outer diameter, said second threaded part coaxial with said first part and separated by a fracture initiating line, each part being provided with a print coaxial with each other, said first part being adapted to permit screwing of said second threaded part into an implant up to a predetermined torque at which said fracture initiating line fractures between the two parts,
    wherein the print provided on said second part is an interior print configured for permitting an optional subsequent unscrewing of said second part, and
    wherein said fracture initiating line and said print of said second part are offset from each other along an axis extending between said first and second coaxial parts.

2. The plug according to claim 1, wherein said second threaded part includes external threads that are configured to be screwed into a tapped hole provided in one of the implants.

3. The plug according to claim 1, wherein said second part includes external threads that terminate adjacent said fracture initiating line.

4. The plug according to claim 1, wherein said second threaded part has a length sized to be embedded in the tapped hole of the implant.

5. The plug according to claim 1, wherein the fracture initiating line is defined by a groove between said first part and said second part having a depth calibrated to the magnitude of said predetermined torque.

6. The plug according to claim 1, wherein the print of said first part is an interior print.

7. The plug according to claim 6, wherein said print of said first part is hexalobate.

8. The plug according to claim 1, wherein the print of said first part is an exterior print.

9. The plug according to claim 1, wherein the print of said second part is hexalobate.

10. Plug according to claim 9 wherein the print is hexagonal.

11. The plug according to claim 1, wherein the print of said second part is blind and opens onto a face of said second part which faces toward said first part.

12. A spinal implant set screw comprising a torque head having at least one planar external surface for the external application of torque to said set screw, said planar external surface being parallel to the longitudinal axis of said set screw, and said torque head joined by a torque-limiting area to a screw member having an external threaded area which has an internal torque opening.

13. A spinal implant set screw as set forth in claim 12 wherein said torque-limiting area includes a necked portion.

14. A spinal implant set screw as set forth in claim 12, wherein said torque-limiting area includes an internal opening.

15. A spinal implant set screw as set forth in claim 12, wherein said torque-limiting area includes a reduced cross-sectional area.

16. A spinal implant set screw as set forth in claim 15, wherein said screw member has a high-compression surface.

17. A spinal implant set screw as set forth in claim 16, wherein said high-compression surface has at least one point.

18. A spinal implant set screw as set forth in claim 17, wherein said screw member has a bevel and a lateral surface with at least one projecting point.

19. A spinal implant set screw as set forth in claim 18, wherein said torque head has an external hexagonal cross-section.

20. A spinal implant set screw as set forth in claim 12, wherein said internal torque opening comprises means for cooperating with a tool.

21. An orthopedic set screw comprising:
    a torque head having at least one external planar surface for the external application of torque;
    a screw member having external threads and a longitudinal axis; and
    a torque-limiting area joining said torque head and said screw member, said external surface being parallel to the longitudinal axis of said screw member and said torque-limiting area being an area of reduced external diameter and including a central opening, said screw member including a torque applicator opening adjacent said central opening and internal to said external threads and including an external, high-compression, rod-contacting surface.

22. An orthopedic set screw as set forth in claim 21, wherein said set screw is formed of a biocompatible metal.

23. An orthopedic set screw as set forth in claim 22, wherein said torque applicator head has an external cross-sectional hexagonal shape and said torque applicator opening has an internal hexagonal cross-section.

24. A surgical screw comprising:
    a first threaded portion having a longitudinal axis and a terminal surface with at least one point, and an axially aligned second portion with a hexagonal-shaped external configuration, said screw having an opening along said longitudinal axis which is hexagonal-shaped in at least said first threaded portion.

25. A spinal implant system comprising:
    a rod;
    a member which cooperates with said rod and having a threaded bore; and
    a set screw having a longitudinal axis and which is received in said threaded bore to secure said rod relative to said member and including a hexagonal shaped torque head having a first diameter joined by a torque-limiting area to a screw member having external threads of a second diameter, said torque-limiting area having a third diameter which is smaller than the first diameter and smaller than the second diameter, the torque-limiting area having a central opening, said screw member including a hexagonal shaped torque applicator opening joined to said central opening and internal to said externally threaded area.

26. A spinal implant system comprising:
    a rod;
    an anchor which cooperates with said rod and has a threaded bore; and
    a set screw which is received in said threaded bore to secure said rod relative to said anchor, said set screw having a longitudinal axis and having along said axis a torque head, a torque-limiting area, and an externally threaded area which includes a terminal high compression rod-contacting surface, said torque-limiting area having a smaller external diameter than said torque head, and said torque head extending axially outward relative to said threaded bore, said set screw further comprising an internal torque opening extending along said longitudinal axis through said torque head and said torque-limiting area into said externally threaded area.

27. A spinal implant system according to claim 26, wherein said torque head is an external torque head.

28. A spinal implant system according to claim 27, wherein said external torque head comprises a head having an external hexagonal cross-section.

29. A spinal implant system according to claim 26, wherein said internal torque opening comprises a hexagonal opening.

30. A spinal implant system according to claim 26, which comprises a biocompatible, surgical-grade metal.

31. A threaded plug, comprising:
a head including an upper portion having a first outer diameter and defining a tool cooperating surface for application of torque, and a lower portion having a second outer diameter;
a screw member having external threads and having a third outer diameter; and
a torque-limiting area including a central opening, said torque-limiting area joining said lower portion of said head and said screw member,
wherein said screw member includes a torque applicator opening adjacent said central opening and internal to said external threads, and
further wherein said first outer diameter is larger than said third outer diameter and said third outer diameter is larger than said second outer diameter, whereby at least a part of said lower portion may extend into an internally threaded opening adapted to receive said screw member.

32. The plug of claim 31, wherein said lower portion is substantially cylindrical.

33. The plug of claim 31, wherein said tool receiving surface of said head is an internal print.

34. The plug of claim 33, wherein said internal print is six sided.

35. The plug of claim 34, wherein said internal print is hexalobate.

36. The plug of claim 31, wherein said torque applicator opening of said screw member is hexalobate.

37. A threaded plug, comprising:
an externally threaded part having a first outer diameter and having an axis, said externally threaded part defining an internal print adapted to cooperate with a tool;
a head having a non-threaded outer surface defining a second outer diameter, said head defining a second internal print adapted to cooperate with a driving tool, said head co-axial with said externally threaded part, and said first diameter greater than or equal to said second diameter; and
a torque-limiting area joining said externally threaded part and said head.

38. The threaded plug of claim 37, wherein said first print is hexalobate.

39. The threaded plug of claim 37, wherein said second print is hexalobate.

40. The threaded plug of claim 37, wherein said non-threaded external surface of said head is cylindrical.

\* \* \* \* \*